(12) United States Patent
Johnsson et al.

(10) Patent No.: US 8,182,834 B2
(45) Date of Patent: May 22, 2012

(54) TERNARY NON-LAMELLAR LIPID COMPOSITIONS

(75) Inventors: Markus Johnsson, Lund (SE); Predrik Tiberg, Lund (SE)

(73) Assignee: Camurus AB, Lund (SE)

( * ) Notice: Subject to any disclaimer, the term of this patent is extended or adjusted under 35 U.S.C. 154(b) by 798 days.

(21) Appl. No.: 10/586,777

(22) PCT Filed: Jan. 21, 2005

(86) PCT No.: PCT/GB2005/000202
§ 371 (c)(1),
(2), (4) Date: Apr. 11, 2008

(87) PCT Pub. No.: WO2005/070394
PCT Pub. Date: Aug. 4, 2005

(65) Prior Publication Data
US 2008/0206317 A1    Aug. 28, 2008

(30) Foreign Application Priority Data

Jan. 23, 2004 (GB) .................................. 0401515.2
Apr. 7, 2004 (GB) .................................. 0407936.4

(51) Int. Cl.
*A61K 9/127* (2006.01)
(52) U.S. Cl. ....................................................... 424/450
(58) Field of Classification Search .................. None
See application file for complete search history.

(56) References Cited

U.S. PATENT DOCUMENTS

| | | | |
|---|---|---|---|
| 5,807,573 A | 9/1998 | Ljusberg-Wahren et al. | |
| 5,885,613 A | 3/1999 | Holland et al. | |
| 6,482,517 B1 | 11/2002 | Anderson | |
| 6,537,575 B1 * | 3/2003 | Firestone et al. | 424/484 |
| 6,593,294 B1 * | 7/2003 | Baru et al. | 514/13.7 |
| 2007/0110777 A1 | 5/2007 | Joabsson et al. | |
| 2007/0134336 A1 | 6/2007 | Worle et al. | |
| 2007/0231374 A1 | 10/2007 | Tiberg et al. | |

FOREIGN PATENT DOCUMENTS

| | | |
|---|---|---|
| WO | 95/34287 | 12/1995 |
| WO | 96/10392 | 4/1996 |
| WO | 2005/014162 | 2/2005 |
| WO | 2005/027976 | 3/2005 |

OTHER PUBLICATIONS

Barauskas et al., *Self-assembled lipid superstructures: beyond vesicles and liposomes*, Nano Letters, Aug. 2005, vol. 5, No. 8, pp. 1615-1619.
International Search Report for PCT/GB2005/000202 dated Oct. 13, 2005 (3 pages), Author E. Martin.

* cited by examiner

*Primary Examiner* — Robert M Kelly
(74) *Attorney, Agent, or Firm* — Nixon & Vanderhye P.C.

(57) ABSTRACT

The present invention provides a particulate composition including; a) at least 50% of at least one structure forming amphiphile, b) 0 to 40% of at least one structure swelling amphiphile, and c) 2 to 20% of at least one dispersion stabilizing polymeric amphiphile, where all parts are by weight relative to the sum of the weights of a+b+c and wherein the composition comprises non-lamellar particles or forms non-lamellar particles when contacted with an aqueous fluid. Where component b) is 0% then component a) comprises at least two structure forming amphiphiles. The invention also provides pharmaceutical compositions of the compositions and kits containing the compositions for establishing a pharmaceutical formulation of an active agent.

12 Claims, 3 Drawing Sheets

TERNARY NON-LAMELLAR LIPID COMPOSITIONS

This application is the US national phase of international application PCT/GB2005/000202 filed 21 Jan. 2005 which designated the U.S. and claims priority to GB 0401515.2 filed 23 Jan. 2004, and GB 0407936.4 filed 7 Apr. 2004, the entire content of each of which is hereby incorporated by reference.

The present invention relates to the protection, stabilisation, solubilisation and delivery of active agents in pharmaceutical and neutraceutical compositions. In particular, the invention relates to amphiphilic compositions and formulations, and active agent delivery systems based upon these.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ "sponge" phase which comprises a multiply interconnected three-dimensional bi-continuous network of bilayer sheets which lack the long-range order of the liquid crystalline phases. Depending upon their curvature, these phases may be described as normal (mean curvature towards the apolar region) or reversed (mean curvature towards the polar region). Where the spontaneous curvature of the lipid system is close to zero, the structures are typically lamellar, such as uni- or multi-lamellar vesicles/liposomes and where the spontaneous curvature is more negative or positive, micellar, cubic and hexagonal phases typically dominate.

The non-lamellar liquid crystalline and $L_3$ phases are thermodynamically stable systems. That is to say, they are not simply a meta-stable state that will separate and/or reform into layers, lamellar phases or the like, but are the thermodynamically stable form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area between polar and apolar regions. This has led to considerable investigation of non-lamellar phases particularly in controlled-release formulations and for solubilising compounds of relatively low solubility.

As discussed above, a bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk non-miscible phase would cause problems, such as in parenteral applications. Further control of a compound's release profile may also be achieved by such a dispersion of non-lamellar particles.

Liquid crystalline or $L_3$ phase can be in or near thermodynamic equilibrium with the excess solvent and may be dispersed into colloidally stable dispersions of non-lamellar particles. Such particles may be fully (i.e. thermodynamically) stable, or may gradually degrade, thereby providing control over the release profile for active agents formulated therewith. The formation of dispersions can be spontaneous or as the result of mechanical force such as shearing or ultrasound. These non-lamellar particles are of considerable interest in the delivery of active agents and have been proposed as carriers for many such actives.

A method for the formation of dispersed particles of non-lamellar phase in solvents such as water is described in U.S. Pat. No. 5,531,925. Such particles have a non-lamellar liquid crystalline or $L_3$ interior phase and a lamellar or $L_3$ surface phase and may also contain active ingredients.

Known particles of liquid crystalline or $L_3$ interior phase may be formed by methods such as adding to this phase a solution of surface-phase forming agent, stirring to form a coarse dispersion and fragmenting the resulting mixture.

In order to assess the presence of a liquid crystalline phase, the prospective liquid crystalline material may be examined by use of small-angle X-ray diffraction (SAX), cryo-Transmission Electron Microscopy (cryo-TEM) or Nuclear Magnetic Resonance (NMR) spectroscopy studies. The sizes and size distributions of the dispersed particles may be examined by light scattering, particularly by use of laser light scattering instruments.

Dispersions containing active ingredients and particularly those for intravenous administration to the human or animal body are desirably colloidal, that is they should be of a particle size no greater than 10 µm, especially no greater than 5 µm and particularly no greater than 1 µm. If particles within the dispersion exceed this size then the dispersion may not be colloidally stable and there is a considerable risk of causing embolism when the preparation is administered intravenously. Furthermore, it is desirable that the distribution of particle sizes be narrow to maximise control over the release of any active agent. Where a particulate composition is to be administered by a method other than intravenously (e.g. orally, intramuscularly, subcutaneously, rectally or by inhalation), then the particles need not necessarily be colloidal but it remains advantageous to provide a well characterised and reproducible particle size distribution in order to control the rate of decomposition of the particles and/or release of the active agents.

The particle size of a particulate composition should also be stable to storage over a considerable period of time. If the distribution of particle sizes changes significantly then the effective transport rate for composition (e.g. due to diffusion and rate of release of any active agent) may be adversely affected. Of still greater concern is the stability of particle sizes in a colloidal dispersion for intravenous administration. If the particle size distribution of such a dispersion is not stable (e.g. to storage and distribution) then large particles may form over time and be dangerous when administered. Even if not directly dangerous, storage instability can cause significant variability in pharmacokinetics, dynamics and/or efficacy.

In addition to control over particle size, it is desirable to maximise the proportion of particles which are in the desired, non-lamellar, phase in order to maximise the beneficial effects of this in terms of loading capacity, protective encapsulation, controlled release, reproducibility, etc. The proportion of lamellar particles such as uni- or multi-lamellar vesicles should therefore be minimised.

Known methods for the formation of dispersed particles of non-lamellar phase are highly effective, but typically produce a relatively broad distribution of particle sizes and a considerable proportion of "contaminant" lamellar vesicular particles. Increasing the proportion of fragmenting and/or stabilising agent (e.g. surfactant, copolymer and/or protein) in the formulation or increasing the energy input of the homogenisation process may be used to narrow the particle size distribution but at the expense of increasing the proportion of lamellar particles.

One limitation of non-lamellar compositions presently available or suggested is that they frequently rely upon lipids which are not well tolerated in vivo at elevated concentrations. In particular, commonly used monoacyl glycerols (including the popular glyceryl monooleate—GMO) can be toxic if administered (especially parenterally) at high concentrations, which can be dose-limiting. The possibility of toxic side effects from the lipid carrier can also limit the range of indications for which an active agent is used to those of a highly serous nature, where the risk of side-effects may be tolerated. It would, therefore, be a considerable advance to provide lipid compositions which were formable and stable as particulate dispersions, showed predictable non-lamellar phase behaviour and had decreased toxicity, (e.g. as seen from haemolysis indices and/or acute toxicity studies) when compared with widely used compositions (e.g. those including GMO). It would be of further advantage if such formulations were formable and stable as colloidal sized particles (e.g. 0.05 to approximately 2 μm diameter) and had a narrow, mono-modal, particle size distribution.

The present inventors have unexpectedly established that a mixture of at least 3 amphiphilic components comprising a structure forming component, a swelling component and a polymeric component is highly effective in forming stable non-lamellar dispersions and can show surprisingly low toxicity in vivo.

In a first aspect, the present invention therefore provides a particulate composition comprising;
a) at least 50% of at least one structure forming amphiphile,
b) 0 to 40% of at least one structure swelling amphiphile, and
c) 2 to 20% of at least one dispersion stabilising polymeric amphiphile,
wherein all parts are by weight relative to the sum of the weights of a+b+c and wherein the composition comprises non-lamellar particles or forms non-lamellar particles when contacted with an aqueous fluid and wherein if component b) is 0% then component a) comprises at least two structure forming amphiphiles.

Preferred compositions of the present invention additionally contain at least one active agent as described herein and may contain a solvent (particularly water or an aqueous solvent or solvent mixture). The compositions may also contain suitable carriers, excipients, fillers, stabilisers and similar components.

In a preferred aspect, the amphiphilic components of the compositions of the present invention comprise at least 50%, preferably at least 70% and most preferably at least 80% by weight amphiphiles having an aqueous solubility of less than $10^{-5}$ M at 25° C., relative to the total weight of components a+b+c.

In a further aspect, the present invention provides a pharmaceutical formulation comprising at least one composition of the invention and at least one pharmaceutically tolerable carrier or excipient.

The ternary amphiphilic compositions of the invention comprise at least one structure forming amphiphile (component a), either at least one other structure forming amphiphile (component a) or at least one "structure swelling" agent (component b) and at least one dispersion stabilising "polymeric" amphiphilic agent (component c). Components b and c will also facilitate fragmentation of the composition. At least 50% by weight of the total amphiphilic components (a+b+c) should be component a. Preferably this will be 60 to 95%, more preferably 70 to 90%. Correspondingly, component b should be 0 to 40% by weight of a+b+c, especially 2 to 40%, preferably 5 to 30% and more preferably 10 to 25%. Component c should be present at 2 to 20%, preferably 2 to 15% and more preferably 2 to 10% of the total weight of a+b+c.

In the ternary amphiphilic compositions, structure forming component "a" will preferably comprise at least one lipid component selected from phospholipids (e.g phosphatidyl ethanolamines and phosphatidy cholines), glycolipids, and diglycerides. Naturally occurring lipids are particularly suitable and particularly naturally occurring diacyl lipids such as diacyl phosphatidyl ethanolamines, diacylglycerols and diacyl phosphatidyl cholines. Mixtures of phosphatidyl choline and diacyl glycerols are particularly preferred.

Where component b) is absent, then component a) will comprise at least two chemically distinct lipids. It is preferred that this mixture should be of one non-ionic lipid (such as a diacyl glycerol) and one zwitterionic lipid (such as phosphatidyl choline). A particularly preferred mixture is glycerol dioleate (GDO) with soy phosphatidyl choline (SPC).

It is preferred that the structure forming component a) is at least one naturally occurring diacyl lipid and where no component b) is present then component a) is preferably a mixture of at least two naturally occurring diacyl lipids. In a diacyl lipid, the two acyl chains may be the same or different both in terms of chain length and number and type of any unsaturations. Preferred acyl groups have 6 to 32 carbon atoms, preferably 6 to 24 and 0 to 3 unsaturations, especially double bonds. Acyl groups are often described by reference to the number of carbon atoms and the number of unsaturations in the carbon chain. Thus, CX:Z indicates a hydrocarbon chain having X carbon atoms and Z unsaturations. Suitable examples particularly include caproyl (C6:0), capryloyl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. More preferable acyl groups are C14 to C20 groups and most preferably C16 to C18 groups such as palmitoyl (C16:0), palmitoleoyl (C16:1), stearoyl (C18:0), oleoyl (C18:1), elaidoyl (C18:1), linoleoyl (C18:2), linolenoyl (C18:3).

It will be particularly desirable to avoid the use of component b) where the swelling effect upon the non-lamellar structure is undesirable. This may be, for example, where a particular desirable phase, such as hexagonal phase, might not be achieved. This could be due to the effect of one or more other components, such as active agent(s) providing sufficient swelling effect. In one preferred embodiment, therefore, component b) is absent only where at least one additional component, especially an active agent is present.

Component a may also contain up to 10% (e.g. 1-10% by weight of this component) of at least one charged amphiphile, particularly anionic lipids (such as acyl or diacyl phosphatidyl glycerols) or fatty acid (see below). In an alternative preferred embodiment, the charged amphiphile may comprise a cationic amphiphile such as ethylphosphocholine lipids (including 1,2-diacyl-glycero-3-ethylphosphocholines); 1,2-diacyl-3-di- and -tri-alkylammonium-propane lipids (including 1,2-diacyl-3-trimethylammonium-propane); ammonium salts, particularly ternary ammonium halide salts (such as N,N-dioctadecyl-N,N-dimethyl ammonium bromide, N,N-distearyl-N,N-dimethyl ammonium bromide, N-(1,2-dimyristyloxyprop-3-yl)-N-hydroxyethyl-N,N-dimethyl ammonium bromide, N—N-dioleoyl-N,N-dimethyl ammonium chloride and N-(1-(2,3-dioleyloxy)propyl)-N,N,N-trimethyl ammonium chloride, N-(1-(2,3-dioleoyloxy)propyl)-N,N,N-trimethyl ammonium chloride); catioic spermidine derivatives (including 2,3-dioleyloxy-N-[2(sperminecarboxamido)ethyl]-N,N-dimethyl-1-propanaminium trifluoroacetate and diheptadecylamidoglycyl spermidine); and cationic cholesterol derivatives including 3β-(N—(N',N'-dimethylaminoethane)-carbamol) cholesterol.

Correspondingly, 90% or more, preferably at least 95% of the component a should preferably have no net charge under neutral and/or physiological conditions.

In another embodiment, up to 10% by weight (e.g. 1-10%) of component a (preferably 2-7% by weight) may be a physiologically tollerable sterol. Examples of such sterols include animal derived sterols such as cholesterol and plant derived sterols (phytosterols) such as beta-sitosterol, stigmasterol and camposterol). Correspondingly, at least 90% of component a is generally non-sterol in structure, more preferably at least 95%.

Component a should be such that when formulated alone in excess water it forms a reversed non-lamellar phase, preferably a reversed hexagonal phase. This can be easily established for any particular lipid or mixture of lipids proposed as component a by preparing a mixture in water and analysing the phase behaviour by any of the techniques for examining phase behaviour known and/or described herein (including small angle X-ray scattering (SAXS), polarising microscopy and/or cryo-transmission electron microscopy (cryo-TEM)).

Since component a is the dominant component in the composition, it is especially important that this component is biocompatible. Previously, many non-lamellar compositions have relied upon major structure forming components with relatively high acute toxicity, in order to provide the desired ordered structure and stability. By using the compositions of the present invention, the use of lipids with less than ideal biological properties can be reduced or even eliminated.

One measure of the biological activity of a lipid is its solubility in water or aqueous solutions. Components with relatively high aqueous solubilities maintain a higher equilibrium concentration of dissolved lipid monomer in solution and this can be at least partially responsible for the observed biological effects. The commonly used "glycerol monooleate" (GMO), for example, has an equilibrium water solubility of the order of $10^{-7}$ M at room temperature and greater at physiological temperature. In contrast, preferred uncharged lipids for use in "component a" may have a solubility of no more than $10^{-8}$ or more typically $10^{-9}$ M at room temperature, preferably $5 \times 10^{-10}$ M and more preferably $10^{-10}$ M or less. The minimum desirable solubility is generally around $10^{-15}$ M. Table 1 below indicates the equilibrium water solubilities of some structure forming amphiphiles.

A low aqueous solubility is also an advantage in enhancing the stability of the non-lamellar structured particles. In particular, at high dilution, the stability of the non-lamellar system will depend upon the rate at which lipid molecules leave the surface of the structured material and diffuse into solution. The stability of a dispersion of non-lamellar particles will thus be directly related to the solubility of the monomer in the solvent.

TABLE 1

| Lipid | Equilibrium solubility concentration/M | Temp/° C. |
|---|---|---|
| glycerol monooleate | ~$10^{-7}$ | 25 |
| dioleoyl phosphatidyl ethanolamine | ~$10^{-10}$ | 25 |

Where a cationic lipid is included in the compositions of the present invention (e.g. at 1-10% by weight of component a, particularly 2-7% by weight) these compositions are particularly suitable for use in the uptake of nucleic acid into cells. In particular, the compositions of the present invention comprising a cationic lipid are highly suitable for providing transfection of single- or double-stranded nucleic acids such as DNA (e.g. cDNA) or RNA oligomers into cells. Suitable nucleic acid oligomers include small interfering DNAs and RNAs, antisense DNA and/or RNA, plasmids, and single or double stranded DNA or RNA functionally encoding a peptide or protein product (especially where the nucleic acid sequence comprises a functional promoter or start codon as appropriate). In this aspect the active agent of the composition will comprise a nucleic acid, particularly a nucleic acid oligomer.

In a preferred embodiment, the present invention therefore provides a composition of the invention (especially one suitable for transfecting cells with a nucleic acid active agent) wherein the composition comprises a cationic lipid at a level of 1-10% by weight of component a, (particularly 2-7% by weight) and at least one nucleic acid as an active agent. The invention also provides a method for transfecting cells with a nucleic acid (as described herein) comprising administering such a composition.

Compositions of the present invention comprising a nucleic acid active agent (especially in combination with a cationic component) are highly suitable for use in methods of genetic immunisation, gene therapy, anti-sense therapy and nucleic-acid-interference therapy. Where present, the cationic lipid component is thought to modulate the properties of the formulation so as to provide a particularly high level of transfection of the nucleic acid. The nature of the overall composition also provides a protected and encapsulating environment wherein the active agent can partition effectively into the carrier and promotes delivery of the active agent to the desired site of action, as in other embodiments described herein.

The high level of uptake provided by the compositions in the absence of a cationic component may be due to the properties of the compositions including this high level of protection of the active component, controlled delivery in both time and space and enhanced absorption across the biological membrane at the site of action. The further enhancement seen with the inclusion of a cationic component is particularly advantageous and is thought to be due to further increased retention, adhesion and/or fusion at the site of action of the composition.

The swelling component "b" is generally a component which swells the lattice of the amphiphilic structure allowing it to more readily adopt a dispersed particulate form. This component may also facilitate structural transition, for example, from reversed hexagonal to cubic phase structures. The establishment of a suitable swelling agent can be carried out by examining the phase and fragmentation behaviour of mixtures with structure forming lipids using known techniques (including those described herein). Swelling agents will generally have a relatively low molecular weight (e.g. less than 2500, especially less than 2000 and preferably 200 to 1950) and may be components such oligoethylene oxide based surfactants. Preferred examples oligoethylene oxide based surfactants are those having between 5 and 40 ethylene oxide units bonded to a non-polar "tail" group (e.g. as an ester to a fatty acid, such as any of those described herein below, or as an ether to a corresponding fatty alcohol). Preferred examples include, polyoxyethylene fatty acid esters, polyoxyethylene alkylethers, polyoxyethylene sorbitan fatty acid esters (polysorbates), polyoxyethylene sterates, polyoxyethylene castor oil derivatives and polyoxyethylene lipid derivatives. Most preferred examples are TGMO-15 (Nikko), Solutol HS15 (BASF) and polysorbate 80.

The polymeric component "c" is, in general, a component which improves the stability of the dispersion, particularly as colloidal particles. Polymeric components generally have a relatively high molecular weight (e.g. greater than 2000, preferably greater than 2200, more preferably 2500 to 50000, such as 2500 to 10000) and will have at least one polymeric (e.g. copolymeric) portion in their molecular structure. Preferred polymeric components include polyethylene oxide copolymers, lipids derivatised with polyethylene oxide, hydrophobically modified polysaccharides and amphiphilic proteins. Poloxamers as described herein are particularly suitable as the polymeric components as are PEG-substituted lipids, PEG fatty acid esters and PEG-phospholipids including PEG-glyceroldioleate, PEG-dioleoyl phosphatidyl ethanolamine (in particular DOPE-PEG2000 and DOPE PEG-5000) or PEG-dioleoyl phosphatidyl serine.

Preferred examples of polyethylene oxide copolymers are poloxamers, which comprise at least one block of polyoxyethylene and at least one block of polyoxypropylene. The most preferred of these agents are poloxamer 407 (e.g. Pluronic® F127, BASF), poloxamer 188 (e.g. Pluronic® F68, BASF), poloxamer 124 (Pluronic® L44, BASF).

Components b and c act as fragmentation agents and help both in the control and stability of particle phase behaviour and in encouraging and stabilising the fragmentation of the non-lamellar phase into particles. Components b and c will be present at a combined level sufficient to bring about the fragmentation of the structuring agent and/or to stabilise the fragmented non-lamellar phase particles. Such fragmentation may be spontaneous or may require physical fragmentation such as by shearing and/or ultrasonication. The skilled worker will have no difficulty in assessing whether any composition contains sufficient fragmentation agents in view of the Examples herein.

The compositions of the present invention comprise non-lamellar particles or compositions which form such particles on contact with an aqueous fluid. Such a fluid may be a fluid for delivery to a subject (e.g. water or sterile saline) or may be a body fluid, particularly gastric fluid, intestinal fluid, fluid at mucosal surfaces or blood.

As use herein, the term "non-lamellar" is used to indicate a cubic, hexagonal or $L_3$ phase structure or any combination thereof, as opposed to lamellar structures as found in lamellar phase or liposomes. Where a particle is described as having a non-lamellar phase or structure, this indicates that at least the particle interior has this structure. The particles will generally have two distinct regions, an internal region and a surrounding surface region. The surface region, even in a "non-lamellar" particle may be lamellar or crystalline and may be any phase ranging from a highly ordered crystalline or liquid crystal phase to a virtually orderless fluid layer.

The term "lamellar particles" is used herein to indicate vesicular particles (e.g. liposomes) characterised in that they comprise one or more outer lamellar bilayers of amphiphile, surrounding an inner solvent compartment.

In one aspect of the present invention, the compositions comprise non-lamellar particles. This indicates that of the (preferably colloidal) particles present, at least 50%, preferably at least 75% and most preferably at least 85% (as measured by volume) are non-lamellar (e.g. as judged by laser diffraction combined with cryo-TEM or SAXS). In an alternative aspect of the present invention, the compositions form non-lamellar particles on contact with an aqueous fluid. This indicates that upon contact with an aqueous fluid (as described herein) at least 50%, preferably at least 75% and most preferably at least 85% of the particles (as measured by volume) become non-lamellar particles.

In one preferred embodiment of the present invention, the particles comprised or formed by the composition comprise $L_3$ phase, reversed hexagonal phase and/or mixtures thereof. Most preferred is $L_3$ phase.

Where an active agent is formulated in a composition of the invention, the active agent will frequently have an effect upon the phase behaviour of the structuring agent(s). For example, certain active agents (such as cyclosporin A) introduce greater negative curvature than some structuring agents and at high concentrations may cause the formation of highly negatively curved phases, such as the reversed micellar $L_2$ phase rather than a cubic or hexagonal liquid crystalline phase. Nonetheless, such an active agent could be formulated into, for example, a reversed hexagonal phase by formulation with a mixture of components a, b and c having a less negative spontaneous curvature. By this method, the overall mixture provides the appropriate negative curvature to allow use in the compositions of the invention.

The skilled worker will be able to use standard methods to assess the degree of spontaneous curvature of any particular structuring agent (or mixture thereof with other components) or the effect on this by including an active agent. This might be done, for example, by studies of the bulk phase behaviour of each structuring agent in water and subsequent studies with varying concentrations of active agent included. The phases can be examined by any of the methods indicated herein (e.g. polarised light, SAXS, cryo-TEM etc.) and an appropriate blend of components chosen for each case. In some circumstances, where the effect of the active agent on the phase behaviour of the mixture is significant, the structuring agent(s) chosen may not provide the desired non-lamellar phase in themselves (e.g. may have too small or too great spontaneous curvature) but will generate this phase only when also formulated with the active agent. The equilibrium phase may thus change from, for example, cubic to hexagonal liquid crystalline phase upon addition of the active agent.

In a preferred embodiment, the compositions of the present invention comprise at least one active agent. Suitable active agents include human and veterinary drugs and vaccines, diagnostic agents, "alternative" active agents such as plant essential oils, extracts or aromas, cosmetic agents, nutrients, dietary supplements etc. Examples of suitable drugs include antibacterial agents such as β-lactams or macrocyclic peptide antibiotics, anti fungal agents such as polyene macrolides (e.g amphotericin B) or azole antifungals, anticancer and/or anti viral drugs such as nucleoside analogues, paclitaxel, and derivatives thereof, anti inflammatories, such as non-steroidal anti inflammatory drugs, cardiovascular drugs including cholesterol lowering and blood-pressure lowing agents, analgesics, anesthetics, antidepressants including serotonin uptake inhibitors, vaccines and bone modulators. Diagnostic agents include radionuclide labelled compounds and contrast agents including X-ray, ultrasound and MRI contrast enhancing agents. Nutrients include vitamins, coenzymes, dietary supplements etc. The active agents for use in the present invention will generally not be any of components a, b, or c as described herein.

Preferred active agents include human and veterinary drugs selected from the group consisting of peptides such as adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, peptide T and its related peptides, calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, fibronectin fragments and their related peptides, gastrointestinal peptides, growth hormone releasing peptides, immunostimulating peptides, insulins and insulin-like growth factors, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides, substance P and its related peptides, transforming growth factors (TGF) and their related peptides, tumour necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons, interleukins, leptins, leukemia inhibitory factors, stem cell factors, transforming growth factors and tumour necrosis factors; selected from the group consisting of antivirals, steroidal antiinflammatory drugs (SAID), non-steroidal anti-inflammatory drugs (NSAID), antibiotics, antifungals, antivirals, vitamins, hormones, retinoic acid, prostaglandins, prostacyclins, anticancer drugs, antimetabolic drugs, miotics, cholinergics, adrenergic antagonists, anticonvulsants, antianxiety agents, tranquilizers, antidepressants, anesthetics, analgesics, anabolic steroids, estrogens, progesterones, glycosaminoglycans, polynucleotides, immunosuppressants and immunostimulants, cardiovascular drugs including lipid lowering agents and blood-pressure lowering agents, bone modulators; vaccines, vaccine adjuvants, immunoglobulins and antisera; diagnostic agents; cosmetic agents, sunscreens and self-tanning agents; nutrients; dietary supplements; herbicides, pesticides, and repellents. Further examples of active agents can be found for instance in Martindale, The Extra Pharmacopoeia. Suitable loadings for the active agents will, be established by reference to their known doses, bearing in mind the route of administration and that the compositions of the invention may provide a greater biological uptake of active agent than known formulations.

In colloidal compositions, the average particle size will typically be in the range 0.1 to 0.6 µm, for example as determined by light scattering methods (e.g. laser diffraction). Preferably, no more than 1% of particles will be outside the range 0.05 to 1.5 µm, more preferably, not more than 0.1% will be outside this range, and most preferably no detectable (by laser diffraction) proportion of particles will be outside this range. In non-colloidal formulations the average particle size will typically be in the range 10 to 200 µm.

Furthermore, the colloidal formulations of the present invention are typically physically stable to storage over extended periods at ambient temperature. Such formulations should be essentially stable both in terms of phase behaviour and particle size for periods of at least 10 days at room temperature, more typically at least 3 months, preferably at least 6 months and more preferably 12 months or more. In contrast, known dispersions of similar particle size may have particle sizes stable for less than 10 days at room temperature. This is a particular advantage of compositions of the present invention comprising components a+b+c, since compositions of components a+b in the absence of component c are typically less stable to storage.

A particle size distribution can be considered essentially stable to storage if the mode particle size increases no more than two fold during the storage period. Preferably, the mean size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period. In a highly preferred embodiment, the particle size distribution of the compositions of the invention alters in mean particle size and particle size distribution width at half-height by no more than 10% and remains monomodal on storage for the periods indicated above.

It is particularly important in the case of colloidal dispersions for use in intravenous or intra-arterial administration that the particle size distribution be stable during storage and use. A composition containing even a relatively small component of non-colloidal particles may cause embolism, or at least unpredictable rates of release upon administration directly to the blood stream. Similarly, the controlled release of an active agent may be dependent upon a reliable particle size distribution in a composition for administration by any other route. Pharmaceutical, diagnostic and veterinary products are also desirably stable to storage for several months or the cost and availability of the product is significantly adversely affected.

In addition to being highly stable to storage, both in terms of phase behaviour and particle size, the compositions of the present invention are surprisingly and advantageously non-toxic. This low toxicity may be demonstrated, for example, by the lack of heamolytic effect. In a further preferred embodiment, the present invention thus provides compositions and formulations as described herein which are non-heamolytic to a concentration of 0.2% by weight total amphiphile. Preferably the compositions will be non-heamolytic to a total amphiphile concentration of 0.5% and most preferably to a concentration of 1% by weight.

A further demonstration of low toxicity is lack of pyrogenicity and in a further embodiment the present invention further provides compositions and formulations as described herein which are non-pyrogenic in rabbit up to doses of at least 1 ml/kg of 5 wt % solution total amphiphile, preferably at least 2 ml/kg of 5 wt % solution and most preferably at least 5 ml/kg at 5 wt %.

A yet further demonstration of low toxicity is lack of acute toxicity and in a further embodiment the present invention thus further provides compositions and formulations as described herein which show no acute toxicity in rat up to doses of at least 2 ml/kg of 10 wt % solution of total amphiphile, preferably at least 5 ml/kg of 10 wt % solution and most preferably at least 10 ml/kg at 10 wt %.

The compositions of the present invention may be formed by preparing a dispersion of components a, b, and c in a solvent (such as an aqueous solvent) and then optionally treating the dispersion with one or more cycles of heating and cooling. Dispersions of particles comprising components a, b and c are formed as pre-formulations prior to the optional heat treatment cycles. This pre-formulation may be prepared by established methods, such as those indicated in the present Examples and in U.S. Pat. No. 5,531,925, WO 02/02716, WO 02/068561, WO 02/066014 and WO 02/068562 and may itself be a composition of the invention. The disclosures of these and all references cited herein are hereby incorporated herein by reference. Such methods include:

i) Adding an amphiphile/water liquid crystal phase (such as component a in water) to an aqueous solution of fragmentation agent (such as components b and/or c) and either allowing natural fragmentation of the mixture or accelerating the process with, for example, mechanical agitation, vortexing, roto-stator mixing, high-pressure homogenization, microfluidisation and/or ultrasound; or
ii) Adding a mixture of a+b+c (optionally containing at least one bioactive agent) to a solvent (e.g. aqueous solution) and agitating directly.

A further method by which dispersion containing active agents may be prepared, particularly from liquid crystalline phases, is by dissolution in super-critical carbon dioxide (sc-$CO_2$) or an alternative processing solvent, such as light alcohols (e.g methanol or ethanol), suitable for dissolving and lowering the viscosity of the composition. In particular, liquid crystalline phase, such as bulk cubic or hexagonal phase, is often highly viscous and can be difficult to handle and mix. Consequently, if the liquid crystalline phase is to be prepared as a bulk liquid and subsequently loaded with active agent, the mixing required to provide even distribution of the active agent is difficult to achieve. In the super-critical region of the pressure/temperature diagram (typically at room temperature or above and at 150 bar or greater), carbon dioxide forms a highly effective solvent and may be used to reduce the viscosity of the liquid crystalline phase and promote effective mixing and loading with active agents. The sc-$CO_2$ may then be removed (e.g. by reducing the pressure) and the loaded bulk phase dispersed in solvent, as discussed above. The use of sc-$CO_2$ in formation of active-agent loaded dispersed liquid crystalline phases (especially those of the present invention) thus forms a further aspect of the invention.

The phase behaviour and size distribution of particulate formulations of the invention may be controlled by one or more (preferably one) cycles of heating and cooling. Such cycles can be used to convert lamellar particles to non-lamellar form, and/or to reduce the spread of particle sizes. The stability of the particles may also be improved by this method.

A heat cycle brings the composition, with or without the active agent present, up to a temperature sufficient to provide conversion of at least a portion of the particles to non-lamellar phase upon cooling to ambient temperature. This will typically involve heating to around 90-150° C. for 1-30 min followed by cooling to ambient temperature. More typically a heat cycle will involve heating to 100-120° C. for 2-20 minutes before cooling. The most suitable conditions will vary in detail between compositions but will be readily established by the skilled worker.

In the heat cycling process, the mean particle size typically increases slightly but the particle size distribution is reduced.

The presence of particles in non-lamellar form will preferably be assessed from a set of cryo-transmission electron microscopy particle images, preferably showing a sample of more than 20, preferably more than 50 particles. The presence of non-lamellar particles may also be assessed by X-ray scattering experiments.

Since the heat treatment method can be used to convert lamellar particles to non-lamellar form, it is not essential that the pre-formulation particles be non-lamellar. Thus, any of the well-known methods for formulating lipids into vesicles may be used to create pre-formulations for use in heat treatment methods of the present invention. Suitable methods include, for example, sonication or extrusion (such as through a polycarbonate membrane). Such methods will be well known to those of skill in the appropriate art.

The pre-formulations should, preferably, be formulated such that the thermodynamically stable state at ambient temperature is non-lamellar. Alternatively, the non-lamellar form may be a thermodynamically meta-stable state. Where present, the active agent may be incorporated into the particles prior to and/or after heat cycling. Where more than one heat cycle is used, the active agent may be incorporated between cycles. Where the active agent is heat sensitive (e.g. peptide or protein) the active agent is preferably incorporated after heat cycling is complete.

Further control over particle size distribution of a composition of the invention may be provided by forming and/or suspending the particles in an aqueous medium of controlled ionic strength. In particular, small (e.g. colloidal, especially small colloidal (<0.3 μm)) particles are most easily formed by heat treatment at low ionic strength, such as below or around 1 mM NaCl in water. The proportion of non-lamellar particles (i.e. having a non-lamellar core as described herein) is increased by use of the heat cycling method described herein. The particle size distribution may be controlled by heat treatment in a medium (generally an aqueous solution) of controlled ionic strength. The average particle size is generally increased by use of media with higher ionic strength. Typically, stable, non-lamellar particle dispersions may be formed by carrying out the heat treatment step at ionic strength in the range 0.1 mM to 100 mM NaCl (or ionic strength equivalent) depending upon the composition used. The precise size distribution will depend upon the composition and suitable conditions may quickly be established by reference to the methods described herein, but typically sub-micron particles are formed at low ionic strength and larger colloidal and non-colloidal particles at increasing ionic strengths.

Where small particles are required in solutions of relatively high salt concentrations (e.g. in 0.9% NaCl for injections) the particles may be formed by heat treatment at a low ionic strength and further salt(s) added after cooling to provide the desired osmolality.

Furthermore, where a proportion of a charged lipid is included in the amphiphilic components of a composition, (such as up to 10% of component a) it is desirable to conduct heat treatment step at an ionic strength of around 0.1-20 mM NaCl, or an equivalent level of other suitable salt(s). By doing so, the proportion of particles converted to non-lamellar form is increased while maintaining the particle size in a desirable size range.

The particles (which may have been heat treated or may be subsequently heat treated) may be concentrated (e.g. by ultrafiltration or dialysis) and/or dried, for example by spray drying, fluid bed drying or freeze drying. In the case of dried particles, the drying process may be followed by particle size enlargement through single or repeated agglomeration and granulation steps. The concentrated, dried and/or agglomerated particle formulations thus formed may be used as such or hydrated and/or dispersed to yield non-lamellar particle dispersions suitable for use in the delivery of active substances, especially in vivo. Such concentrated, dried and/or agglomerated particle formulations and the dispersions resulting from their re-suspension/hydration form a further aspect of the present invention.

The formulations of the present invention comprise at least one composition of the invention and at least one carrier or excipient. Where the formulation is a pharmaceutical formulation the carriers or excipients will be pharmaceutically tolerable.

The compositions may be formulated with conventional pharmaceutical carriers, diluents and/or excipients such as aqueous carriers (e.g. water for injections), binders, fillers, stabilizers, osmolality adjusting agents, effervescing agents, pH buffers and modifiers, viscosity modifiers, sweeteners, lubricants, emulsifiers, flavours, coating agents (e.g. gastric juice resistant coatings) etc. Formulations comprising a composition of the invention and at least one pharmaceutically acceptable carrier and/or diluent may be formulated in any known dosage form including as suspensions, powders, tablets, capsules, coated capsules, coated tablets, aerosols, suppositories, creams, transdermal patches, sprays etc. Where the composition of the invention has been dried, this may be formulated as a suitable form (such as a powder) for resuspension in an appropriate medium (such as purified water or a solution of physiological osmolality) prior to administration. The formulations may be administered by any suitable method including orally, parenterally (e.g by intramuscular, subcutaneous or intravenous injection or infusion), topically, rectally etc.

The compositions of the present invention have no, or limited toxic effects, provide advantageous properties for the delivery of active agents in vivo and may easily be loaded with such agents. The compositions are thus highly suitable for establishing a suitable or improved delivery system for new or known active agents.

In a still further aspect, the present invention provides a kit suitable for establishing a biologically tolerable formulation of an active agent comprising at least one composition of the present invention. The kit preferably provides a plurality of compositions of the present invention for comparison, such as two, three, four or more. More preferably such a kit will contain at least 10 different compositions of the present invention, which may be presented in an array format such as in the wells of at least one multi-well plate. Such a kit may also include instructions for the loading of the compositions with an active agent and/or their formulation for administration.

The invention will now be further illustrated by reference to the following non-limiting Examples and the attached Figures, in which.

EXAMPLE 1

Amphiphilic Particles 1.1—Preparation of a Non-Lamellar Dispersion

A coarse dispersion of cubic and lamellar particles was formed by mixing DOPE (Avanti Polar Lipids U.S.A., 0.75 g), TGMO-15 (Nikko Japan, 0.2 g) and DOPE-PEG(5000) (Avanti Polar Lipids U.S.A., 0.05 g) in deionized water (49.0 g). The mixture was freeze-thawed 3 times including freezing at −85° C. and thawing under vigorous stirring and shaking at ambient temperature. The resulting coarse dispersion was thereafter homogenised in a microfluidizer at high pressure (350 bar) for 10 min (8 passes) at ambient temperature.

The particle size was measured using laser diffraction (Coulter LS230) after homogenisation.

The homogenised sample was a turbid to bluish colloidal dispersion with particle sizes between 0.05 and 1 micron consisting of cubic phase particles and vesicles.

1.2—Heat Treatment

An optional cycle of heat treatment was carried out on the dispersion prepared in Example 1.1.

A sample of the dispersion generated in Example 1.1 (25 mL) was autoclaved (120° C., 20 min) and cooled to room temperature. When examined by cryo-TEM, a still greater proportion of the particles in the dispersion showed non-lamellar character. The particle size distribution was also somewhat narrowed in comparison with the dispersion prior to heat treatment and shows better storage stability.

Components:
a DOPE
b TGMO-15 (glycerylmonooleate-PEG(15), Nikko, Japan)
c DOPE-PEG(5000)

| Formulation | a:b:c | abc wt % | aqueous medium | aq wt % | Phase before | Temp ° C. | Time min | Phase after |
|---|---|---|---|---|---|---|---|---|
| i | 75:20:5 | 2 | water | 98 | lam/cubic* | 120 | 20 | cubic** |

Figure 1:
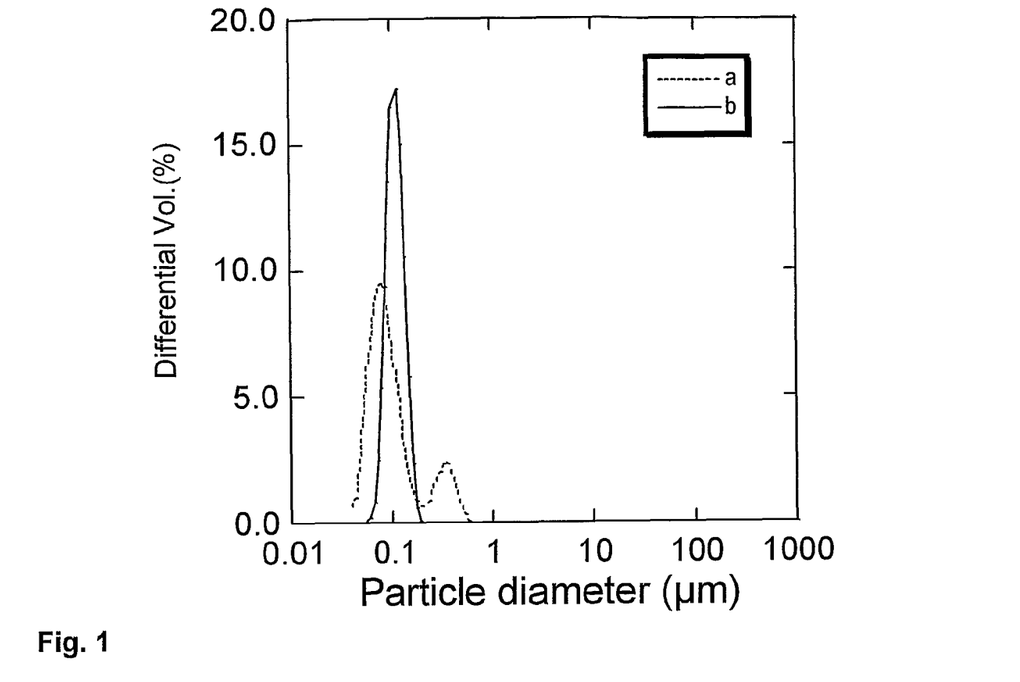
FIG. 1 shows the particle size distribution of a composition of DOPE/TGMO-15/DOPE-PEG(5000) before and after optional heat treatment.

*lam/cubic = mixed cubic and lamellar particles
**cubic = predominantly cubic particles The particle size distribution of the composition before and after heat treatment is shown in FIG. 1.

EXAMPLE 2

Further Composition

The effect of ionic strength during heat treatment was considered by preparing a second composition by the methods of Examples 1.1 and 1.2. The same components a, b and c were used but at a different weight ratio and 3 mM NaCl was used in place of water for the heat treatment step.

| Formulation | a:b:c | abc wt % | aqueous medium | aq wt % | Phase before | Temp ° C. | Time min | Phase after |
|---|---|---|---|---|---|---|---|---|
| ii | 77.2:20.3:2.5 | 2 | 3 mM NaCl | 98 | lam/cubic* | 120 | 20 | cubic* |

Figure 2:
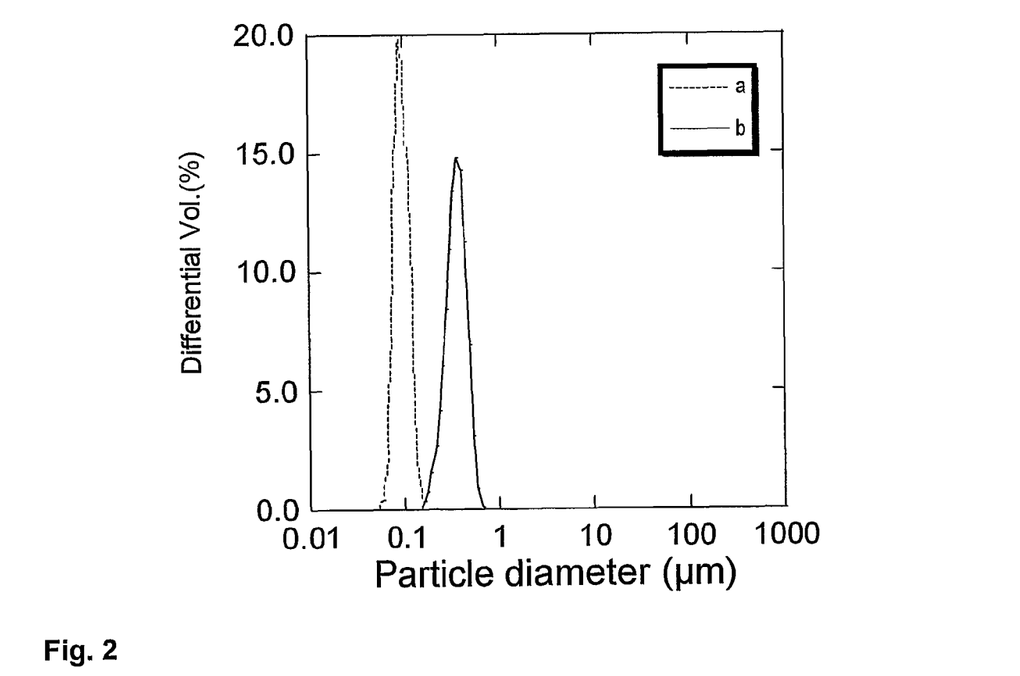
FIG. 2 shows the particle size distribution of a composition of DOPE/TGMO-15/DOPE-PEG(5000) prepared in NaCl solution, before and after optional heat treatment.

The particle size distribution before and after heat treatment is indicated in FIG. 2. In this case, the effect of the higher ionic strength is seen to cause the mode particle size to increase around four-fold while maintaining a narrow particle size distribution. The particles were also converted to essentially 100% cubic phase particles.

EXAMPLE 3

Further Composition

Figure 3:
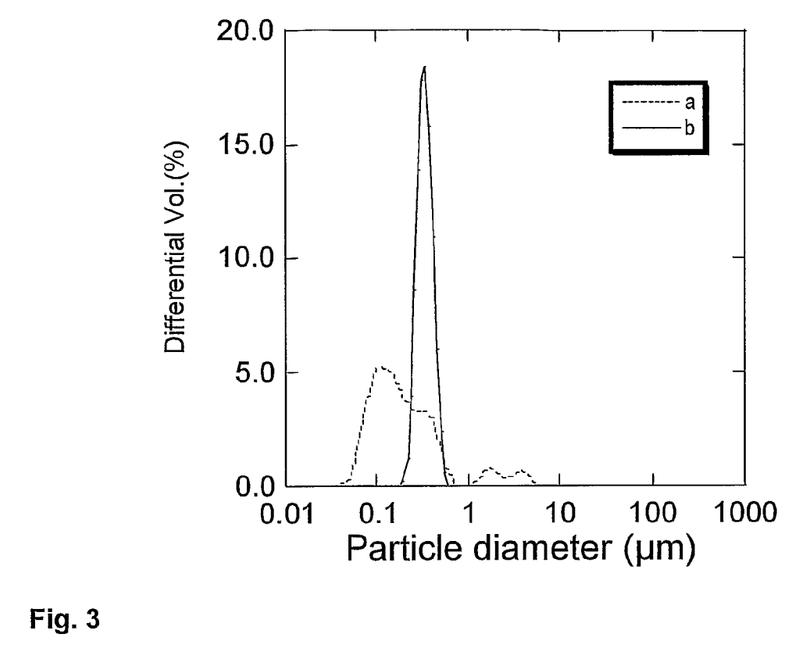
FIG. 3 shows the particle size distribution of a composition of DOPE/Polysorbate 80/Pluronic® F127, before and after optional heat treatment.

A dispersion of DOPE (0.80 g), Polysorbate 80 (0.134 g) and Pluronic® F127 (0.10 g) in deionized water (49.0 g) was prepared by the methods of Examples 1.1 and 1.2. The particle size distribution measured before and after heat treatment is indicated in FIG. 3. The heat treatment is seen to transform the original particles exhibiting a broad multi-modal size distribution into particles with a mono-modal narrow size distribution. The proportion of cubic phase particles in the dispersion was increased to nearly 100% after the heat treatment.

Components:
a DOPE
b Polysorbate 80
c Pluronic® F127

| Formulation | a:b:c | abc wt % | aqueous medium | aq wt % | Phase before | Temp ° C. | Time min | Phase after |
|---|---|---|---|---|---|---|---|---|
| iii | 77.4:13.0:9.6 | 2 | water | 98 | lam/cubic* | 120 | 20 | cubic* |

EXAMPLE 4

Further Composition

Including Anionic Phospholipid

Figure 4:
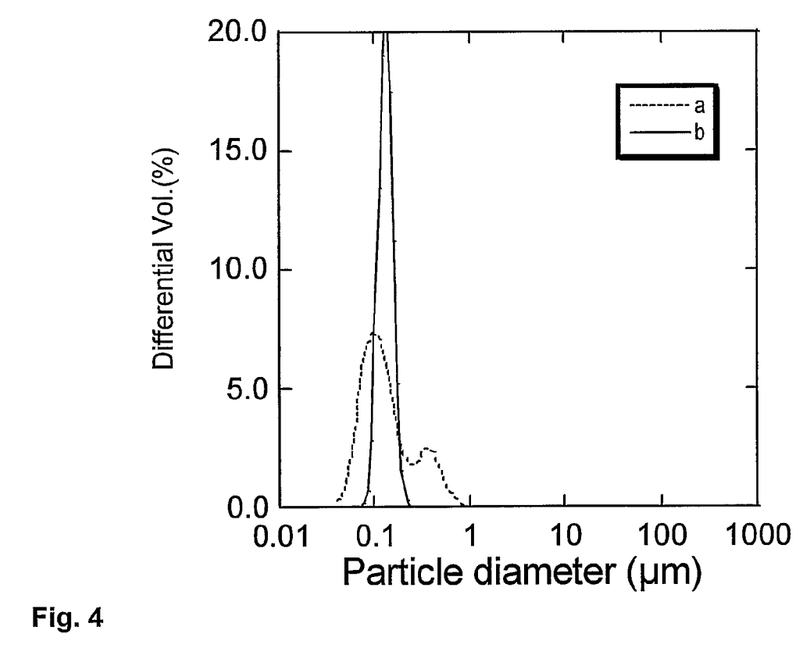
FIG. 4 shows the particle size distribution of a composition of DOPE/DOPG/TGMO-15/DOPE-PEG(5000), before and after optional heat treatment.

A dispersion of DOPE (0.90 g), DOPG (0.036 g), TGMO-15 (0.207 g) and DOPE-PEG(5000) (0.06 g) in deionized water (58.8 g) was prepared by the methods of Examples 1.1 and 1.2. The heat treatment was performed in 5 mM NaCl resulting in a mono-modal narrow size distribution. The particle size distribution measured before and after heat treatment is indicated in FIG. 4. The heat treatment was also accompanied by a turbidity increase of the sample indicating that a greater proportion of the particles in the dispersion were of non-lamellar character.

Components:
a1 DOPE
a2 DOPG
b TGMO-15
c DOPE-PEG(5000)

| Formulation | a1:a2:b:c | abc wt % | aqueous medium | aq wt % | Phase before | Temp ° C. | Time min | Phase after |
|---|---|---|---|---|---|---|---|---|
| iv | 75:3:17:5 | 2 | 5 mM NaCl | 98 | lam/cubic* | 120 | 20 | cubic** |

EXAMPLE 5

Further Composition

Including Anionic Phospholipid

Figure 5:
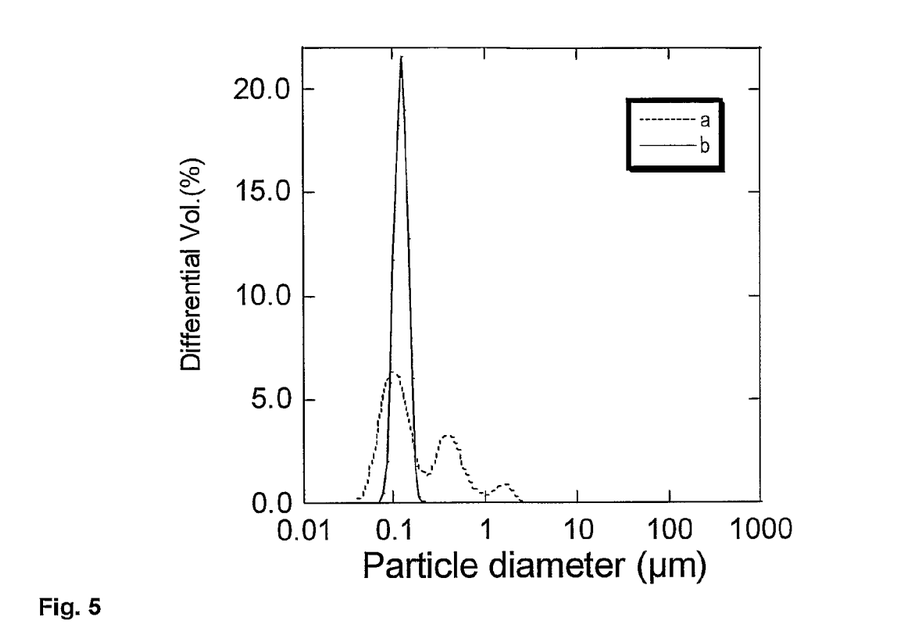
FIG. 5 shows the particle size distribution of a composition of DOPE/DOPG/Polysorbate 80/DOPE-PEG(5000), before and after optional heat treatment.

A dispersion of DOPE (0.90 g), DOPG (0.036 g), Polysorbate 80 (0.212 g) and DOPE-PEG(5000) (0.06 g) in deionized water (58.8 g) was prepared by the methods of Examples 1.1 and 1.2. The heat treatment was performed in 5 mM NaCl resulting in a mono-modal narrow size distribution. The par ticle size distribution measured before and after heat treatment is indicated in FIG. 5. A greater proportion of the particles in the dispersion showed non-lamellar character after the heat treatment.

Components:
a1 DOPE
a2 DOPG
b Polysorbate 80
c DOPE-PEG(5000)

| Formulation | a1:a2:b:c | abc wt % | aqueous medium | aq wt % | Phase before | Temp ° C. | Time min | Phase after |
|---|---|---|---|---|---|---|---|---|
| v | 75:3:17:5 | 2 | 5 mM NaCl | 98 | lam/cubic* | 120 | 20 | cubic** |

EXAMPLE 6

Further Composition

A mixture of Soy PC (Lipoid GmbH, Germany, 0.44 g) and GDO (Danisco, Denmark, 0.44 g) is prepared by mixing in ethanol and subsequently removing the solvent by evaporation. To this mixture, Polysorbate 80 (0.05 g) is added and the amphiphile mixture is mixed to give a homogenous liquid by vortex mixing. The SPC/GDO/P80 mixture (0.93 g) is added to 49 g of de-ionized water containing dissolved DOPE-PEG (5000) (0.07 g). The mixture is shaken for 12 h (350 rpm) and thereafter homogenised and heat-treated according to the methods of Example 1.1 and 1.2.

Components:
a1 Soy PC
a2 GDO
b Polysorbate 80
c DOPE-PEG(5000)

| Formulation | a1:a2:b:c | abc wt % | aqueous medium | aq wt % | Phase before | Temp ° C. | Time min | Phase after |
|---|---|---|---|---|---|---|---|---|
| vi | 44:44:5:7 | 2 | water | 98 | lam/cubic* | 120 | 20 | cubic** |

EXAMPLE 7

Active Agent Loading

Non-lamellar dispersions of varying components in water and saline solutions may be prepared by the method of Example 1.1 and optionally treated with the heat treatment method of Example 1.2.

To the dispersions is added the cationic peptide desmopressin to a concentration of 1 mg/ml. The dispersion is allowed to equilibrate for 60 minutes at room temperature and reanalysed for particle size and optionally phase behaviour. The particle size is not affected as determined using laser diffraction.

EXAMPLE 8

Toxicity Testing 8.1 Heamolysis

Figure 6:
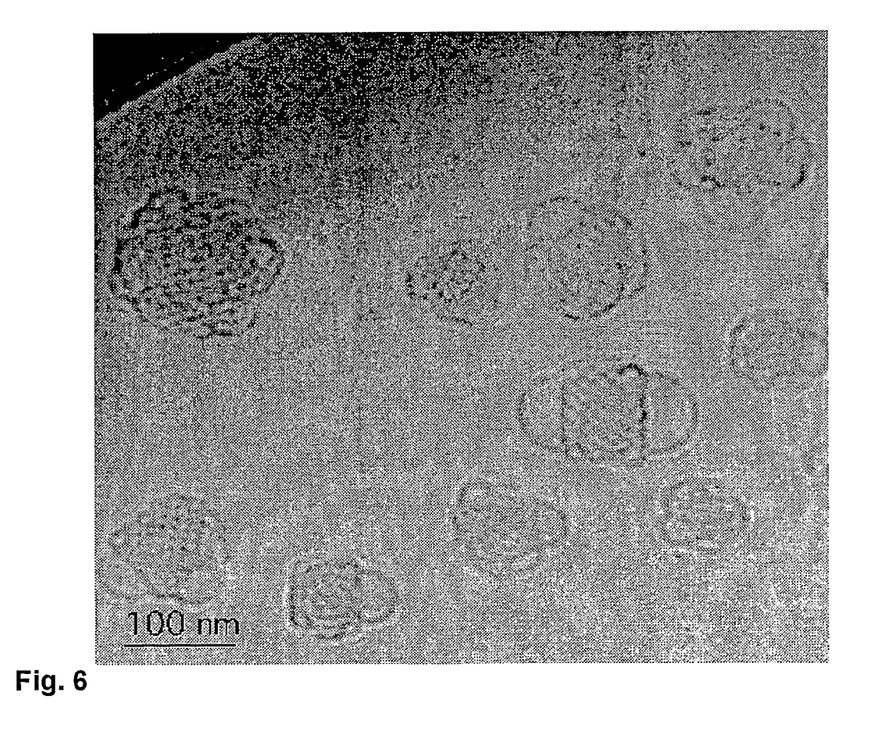
FIG. 6 shows a Cryo-TEM image of non-lamellar particles obtained after heat-treating a homogenisate of DOPE/TGMO-15/DOPE-PEG(5000) (76/20/4).

A cubic phase dispersion was prepared by the methods of Examples 1.1 and 1.2 using the following components:
a) DOPE
b) TGMO-15
b) DOPE-PEG5000 in the weight ratio a:b:c 76:20:4, dispersed in water to a total amphiphile concentration of 5 wt %. This solution was diluted with water to varying final concentrations. A Cryo-TEM image of the dispersion is shown in FIG. 6.

The heamolytic effect of the cubic phase dispersion at varying concentrations was measured. The dispersion was found to be non-heamolytic at concentrations of up to 1 wt % total amphiphile.

Cubic phase dispersions of glycerol monoolein (GMO) were prepared by a corresponding method and tested for haemolytic effect under the same conditions. The GMO based dispersion showed significant haemolytic effects at concentrations as low as 0.1 wt % total amphiphile.

8.2 Pyrogenicity

A DOPE based formulation was prepared as in Example 8.1 and was tested for pyrogenicity in a rabbit model. The composition was found to be non-pyrogenic up to doses of at least 5 ml/kg (5 wt % total amphiphile).

8.3 Acute Toxicity

DOPE and GMO based compositions were prepared as in Example 8.1 and tested for acute toxicity in a rat model.

The DOPE based cubic phase dispersion showed no acute toxicity in a dose dependant study with doses up to 10 ml/kg (10 wt % amphiphile).

The glycerol monolein based cubic phase dispersions, on the other hand, were found to be toxic at corresponding lipid doses.

The invention claimed is:

1. A particulate composition, said composition comprising;
   a) at least 50% of at least one structure forming amphiphile comprising at least one lipid component selected from phospholipids, glycolipids, and diglycerides,
   b) 2 to 40% of at least one structure swelling amphiphile comprising at least one swelling agent selected from polyoxyethylene alkylethers, polyoxyethylene sorbitan fatty acid esters, polyoxyethylene fatty acid esters, polyoxyethylene castor oil derivatives or polyoxyethylene lipid derivatives, and
   c) 2 to 20% of at least one dispersion stabilising polymeric amphiphile comprising at least one polymeric agent selected from poloxamers, PEG-glyceroldioleate, PEG fatty acid esters or PEG-phospholipids,
   wherein all parts are by weight relative to the sum of the weights of a+b+c and wherein the composition comprises non-lamellar particles or forms non-lamellar particles when contacted with an aqueous fluid.

2. A composition as claimed in claim 1 wherein the amphiphilic components comprise at least 50% by weight amphiphiles having an aqueous solubility of less than $10^{-9}$ M at 25° C., relative to the total weight of components a+b+c.

3. A composition as claimed in claim 1 wherein the amphiphilic components comprise at least 70%, by weight amphiphiles having an aqueous solubility of less than $10^{-9}$ M at 25° C., relative to the total weight of components a+b+c.

4. A composition as claimed in claim 1 wherein said non-lamellar particles comprise $L_3$ phase and/or reversed hexagonal phase.

5. A composition as claimed in claim 1 additionally comprising at least one active agent.

6. A composition as claimed in claim 1 wherein component a) comprises a cationic lipid at a level of 1-10% by weight and the composition further comprises at least one nucleic acid active agent.

7. A composition as claimed in claim 1 wherein said non-lamellar particles have a particle size of 10 to 200 µm.

8. A composition as claimed in claim 1 wherein said non-lamellar particles are colloidal.

9. A composition as claimed in claim 8 wherein said non-lamellar particles are stable, both in terms of phase behaviour and particle size, to storage at room temperature for at least 10 days.

10. A composition as claimed in claim 1 which is non-haemolytic up to a concentration of 0.2% total amphiphile.

11. A composition as claimed in claim 1 which is non-haemolytic up to a concentration of 1% total amphiphile.

12. A pharmaceutical formulation comprising at least one composition as claimed in claim 1 and at least one biologically tolerable carrier or excipient.

* * * * *